(12) United States Patent
Müller (10) Patent No.: US 10,377,554 B2
(45) Date of Patent: Aug. 13, 2019

(54) SYRINGE

(71) Applicant: Ivoclar Vivadent AG, Schaan (LI)

(72) Inventor: Frank Müller, Feldkirch (AT)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 14/889,330

(22) PCT Filed: Mar. 13, 2014

(86) PCT No.: PCT/EP2014/054925
§ 371 (c)(1),
(2) Date: Nov. 5, 2015

(87) PCT Pub. No.: WO2014/180591
PCT Pub. Date: Nov. 13, 2014

(65) Prior Publication Data
US 2016/0089216 A1    Mar. 31, 2016

(30) Foreign Application Priority Data
May 7, 2013  (EP) .................................... 13166888

(51) Int. Cl.
*A61C 5/62*    (2017.01)
*A61M 5/24*    (2006.01)
(Continued)

(52) U.S. Cl.
CPC ............ *B65D 83/0033* (2013.01); *A61C 5/62* (2017.02); *A61M 5/2425* (2013.01);
(Continued)

(58) Field of Classification Search
CPC ........... A61C 5/062; A61C 5/064; A61C 5/64; A61C 5/62–68; A61C 5/50; A61C 5/55;
(Continued)

(56) References Cited

U.S. PATENT DOCUMENTS 2,615,447 A * 10/1952 Cohen .................. A61C 9/0026
126/263.07
3,462,840 A * 8/1969 Ellman .................... A61C 5/50
433/217.1
(Continued)

FOREIGN PATENT DOCUMENTS

CA    2304166 A1    4/1999
CA    2383181 A1    11/2002
(Continued)

*Primary Examiner* — Wade Miles
*Assistant Examiner* — Drew S Folgmann
(74) *Attorney, Agent, or Firm* — Ann M. Knab; Thad McMurray (57) ABSTRACT

A syringe, in particular for viscous or liquid dental materials, provided with a syringe housing 12, in which a plunger 22 is guided for displacement in a manner known, wherein the plunger 22 can be removed from the syringe housing 12 and introduced into the syringe housing 12, and with an outlet cannula 20, which is fitted on the syringe housing 12. A region of the syringe housing 12 which is adjacent to the outlet cannula 20 is of deformable design and a region of the syringe housing 12 which is remote from the outlet cannula 20 is of dimensionally stable design.

18 Claims, 4 Drawing Sheets

(51) Int. Cl.
*A61M 5/28* (2006.01)
*A61M 5/31* (2006.01)
*B65D 83/00* (2006.01)

(52) U.S. Cl.
CPC .......... *A61M 5/282* (2013.01); *A61M 5/3129* (2013.01); *A61M 5/3134* (2013.01)

(58) Field of Classification Search
CPC ....... A61C 5/60; A61C 19/005; A61C 9/0026; A61M 2005/1403; A61M 5/3148; A61M 5/178; A61M 5/281; A61M 5/158; A61M 5/282; A61M 5/3129; A61M 5/2425; A61M 5/3134
USPC ............... 222/206, 209, 212, 213, 386, 387; 604/132, 133, 153, 212, 214, 216, 217
See application file for complete search history.

(56) References Cited

U.S. PATENT DOCUMENTS

| | | | |
|---|---|---|---|
| 5,034,003 A * | 7/1991 | Denance | A61M 5/20 604/117 |
| 5,052,403 A * | 10/1991 | Haber | A61B 5/15003 600/578 |
| 2005/0215660 A1 * | 9/2005 | Tomikawa | A61K 6/0023 523/118 |
| 2007/0265579 A1 * | 11/2007 | Kleyman | A61M 5/31501 604/207 |
| 2007/0273331 A1 | 11/2007 | Cross et al. | |
| 2008/0206706 A1 | 8/2008 | Mossle | |
| 2009/0171311 A1 | 7/2009 | Genosar et al. | |
| 2009/0198194 A1 | 8/2009 | Madin et al. | |
| 2010/0254149 A1 | 10/2010 | Gill | |
| 2011/0064977 A1 | 3/2011 | Wendel et al. | |

FOREIGN PATENT DOCUMENTS

| | | | |
|---|---|---|---|
| FR | 2659858 A1 * | 9/1991 | ............. A61M 5/32 |
| JP | 2002200100 A | 7/2002 | |
| JP | 2002236312 A | 8/2002 | |
| JP | 3100119 U | 4/2004 | |
| JP | 2004230122 A | 8/2004 | |
| JP | 2008061469 A | 3/2008 | |
| JP | 2010011668 A | 1/2010 | |

* cited by examiner

SYRINGE

CROSS-REFERENCE TO RELATED APPLICATIONS

This application is a National Stage application of International Patent Application No. PCT/EP2014/054925 filed on Mar. 13, 2014, which claims priority to European Patent Application No. 13 166 888.1 filed on May 7, 2013, the disclosures of which are incorporated herein by reference in their entirety.

TECHNICAL FIELD

The invention concerns a syringe, in particular for liquid or viscous dental materials.

BACKGROUND

Such a syringe 10 has been known for a long time. As an example for this, reference is to be made to the already somewhat newer U.S. Pat. No. 4,863,072. With this syringe, a plunger can be screwed into a syringe housing for squeezing out dental material in order to thus make possible a controlled and precisely controllable output of the dental material.

For a faster output of the dental material, a two-hand operation is possible as well with this solution, wherein the syringe housing is held with one hand or with two fingers of this hand, and the actuation knob there, which is provided in the shape of a disc, is rotated quickly.

In this connection, however, it is regarded as dissatisfactory that the time needed is considerable in case of quick actuation, and a quick actuation requires by a fast manual rotation which is regarded as inconvenient.

A faster output of the local material to be injected is virtually possible only by means of rotating the disc even faster.

Numerous further syringes have already been suggested. As an example, reference is to be made to DE 199 00 792 C1, according to which dosage is to be effected by means of rotating a thumb wheel. This solution is rather complicated and makes necessary also individual parts which are manufactured in such a manner that they are precisely fitting, which leads to correspondingly high production costs.

SUMMARY OF THE INVENTION

In contrast to this, the invention is based on the task of creating a syringe, which makes possible, despite the use of a cost-efficient production process, a fast emptying of the syringe but, if necessary, also fine dosage.

In accordance with the invention, it is particularly favourable that the syringe housing in which the plunger is guided is of solid design over a part of its length, i.e. is inflexible towards the plunger, and is deformable over a great portion of its length, wherein preferably also this portion of the syringe housing can be penetrated by the plunger. By combining these parts, the dental material can be squeezed out quickly according to the choice of the user by pressing on the plunger in a manner known per se and the same being moved translationally, or the deformable portion being squeezed together for fine dosing, such that dental material is squeezed out.

It is to be understood that for the coming into effect of the squeezing out, the thrust resistance of the plunger, i.e. the static friction of the plunger in the syringe housing, is larger than the flow resistance of the dental material through the outlet cannula. This is automatically the case with liquid dental materials anyway, which is, even if the plunger is already positioned in the deformable portion of the syringe housing, i.e. an almost complete emptying has already taken place.

Even with viscous dental materials, it is favourable if the slide resistance of the plunger in the syringe housing, i.e. insofar static friction with the stagnant plunger, is adapted to the viscosity, i.e. with more viscous dental material, a larger degree of static friction is set than with more liquid material.

The setting can be done or set in any suitable manner by means of selecting the dimensions of the plunger on the one hand, and the syringe housing on the other hand. Preferably, the syringe housing is provided with an inside diameter which is slightly, for example 0.2 mm, larger than the outside diameter of the cylindrical plunger. In a manner known per se, the plunger is provided with an annular groove at its front end, i.e. the end which is adjacent to the outlet cannula. In this groove, an O-ring is mounted as well in a manner known per se. The O-ring projects in a radial direction beyond the outside diameter of the plunger, for instance by 0.4 mm. This results in a sealing between the wall of the syringe housing and the plunger whose O-ring is compressed during the process of introduction into the syringe housing, and remains equally compressed over the course of the sliding movement of the plunger.

For example, the annular groove can be provided with a width of 2 mm and a radial depth of 1.6 mm. If an O-ring of a corresponding diameter and a thickness of 2 mm is inserted, this will accordingly project by 2 mm−1.6 mm=0.4 mm in the outward direction, and will be compressed by 0.2 mm when introduced into the syringe housing. The amount of contact pressure determines the slide resistance of the plunger, but also the static friction of the plunger inside the syringe housing.

In order to achieve a larger value for static friction now, it is possible to either insert an O-ring with a thickness of 2.1 mm, or to reduce the depth of the annular groove, for example to 1.5 mm. In both cases, the desired result can be achieved that when the front portion of the syringe housing is compressed, dental material is squeezed out of the outlet cannula, wherein the squeezing out does not lead to a backwards movement of the plunger.

Special attention is paid, in accordance with the invention, to the guidance of the plunger inside the front, i.e. the flexible, portion of the syringe housing. For instance, it is possible to put the flexible portion of the syringe housing into practice in the manner of a grip recess only at two regions of the syringe housing which are positioned opposite of each other, and leave the syringe housing otherwise to extend in a dimensionally stable design up to the outlet cannula.

In any case, the dimensioning is effected in such a manner that an "overflow", i.e. a movement of dental material beyond the sealing of the plunger, is safely prevented. Here as well it holds true that the relative dimensions of the plunger on the one hand, and of the syringe housing on the other hand, can be adapted to the degree of viscosity of the dental material. With liquid dental material, no special preparations need to be made typically, since the liquid dental material can be easily squeezed out through the outlet cannula when the regions of the deformable portion of the syringe housing that are positioned opposite of each other are compressed.

With more viscous dental material, it may be favourable if the elasticity of the easily deformable region of the syringe housing is made use of in order to increase the contact pressure. For this purpose, the syringe housing may be manufactured—for instance, by means of thermal contraction—with an undersize there, such that the sealing does then not only have to be compressed there by 0.2 mm, for example, but rather by 0.3 mm if the plunger is supposed to enter into the deformable region of the syringe housing.

In accordance with the invention, it is particularly favourable if the deformable region of the syringe housing is positioned adjacent to the outlet cannula. Due to this, it is first achieved that the fine dosage is available also when the plunger has moved over more than half towards the outlet end, i.e. the syringe has, for example, been half emptied. The deformable region can, for instance, cover the front quarter or the front fifth of the cylindrical portion of the syringe housing. The syringe housing can then also be compressed if the plunger has already extended slightly into the deformable region, namely in that merely the portion of the deformable region which is adjacent to the outlet cannula is then compressed.

It is to be understood that especially with a viscous dental material, the deformable region does not typically spring back after pressure actuation. This is favourable for thus an inhalation through the outlet cannula is prevented, which would otherwise cause pollutions. Rather, the deformable region is only brought back to its nominal dimensions, i.e. pressed apart, when the pressure rod of the plunger is further actuated.

Insofar, no particular spring features of the deformable region of the syringe housing are necessary or desired, whereas, in contrast, its limited degree of deformability is.

The deformability of the front region of the syringe housing can be adapted to the requirements to a great extent, and can be designed in accordance with the preferences of the user. Such, it is possible, for example, to manufacture a syringe housing which consists of a hard plastics material as a cylinder which is provided with two reach-through recesses at its front portion. Into this outer housing, an inner housing of the syringe housing can then be inserted and can be fitted at the desired position. The inner housing then covers the windows in the outer housing, and the syringe housing is then flexible and deformable at this position. The plunger can then penetrate the inner housing over its entire cylindrical length, and the outlet cannula is then typically formed in one piece on the inner housing.

This solution has the advantage that the plunger can be guided up to the front end of the cylindrical portion of the inner housing, such that no or very small residues of the comparatively expensive dental material remain inside the syringe when it is emptied.

Alternatively and with the same advantages, the outer housing can also be guided to the very front, and by means of providing tongues, the outer housing can itself be put into practice in deformable design. By exerting pressure on the tongues of the outer housing, the inner housing is then compressed, and the finely dosed output of dental material is made possible.

In accordance with another embodiment of the invention, the plunger is connected with a lathe spindle in a manner known per se. The syringe housing is provided with an internal thread, and the lathe spindle guides the plunger with the help of the rotational movement of the turning handle of the lathe spindle for squeezing out the dental material. This solution basically allows already a finer dosage than syringes with which a plunger is guided in a purely translational manner.

Yet it is favourable, in accordance with the invention, to provide a deformable region of the syringe housing, which adjoins in the direction towards the front, i.e. towards the outlet cannula, and at which dental material is squeezed out by means of slight compression of the walling of the syringe housing. This fine dosage can be effected quickly and pointedly, and also with visual and sensorial control.

In accordance with another, particularly preferred embodiment, the deformable region is arranged in the course of the outlet cannula itself. With this embodiment, the deformable region is provided in the manner of a pump, i.e. it is typically provided with two back-pressure valves, one in front of and one behind the membrane of the pump, such that, when the deformable region arranged there is compressed, the material is squeezed towards the front, which is done independently of the static friction of the plunger inside the cylindrical portion of the syringe housing.

The advantage of this embodiment is that the pressure acting as a result of pressure onto elastic portion 50 inside the syringe conveys the dental material out of cannula 20 through front valve 82.

When the pressure exerted by the finger onto elastic region 50 is released, an equalization of pressure is effected in the region of pump housing 84 by means of inhalation of dental material through the back valve 80 which is positioned nearer towards plunger 22. As a result, a syringe in accordance with this design is automatically ready for conveyance again after each actuation, without the need to additionally actuate tappet 42. The syringe is insofar self-priming.

The cleaning effort for the plunger can therefore be kept at a minimum. For instance, the friction between the plunger and the inner wall of the syringe can be set to low values for this purpose, which overall increases the comfort of operation.

In another advantageous embodiment, it is intended to provide the deformable region or at least a part of the deformable region of the syringe housing as transparent or translucent. As a result of this measure known per se, a visual control of the condition of the syringe, and also the remaining dental material, can be put into practice easily.

[Here Follow the Advantages of the Subordinate Claims]

BRIEF DESCRIPTION OF THE DRAWINGS

Further advantages, details and features result from the subsequent description of several embodiments with the help of the Figures, which show.

DETAILED DESCRIPTION OF THE INVENTION

Figure 1:
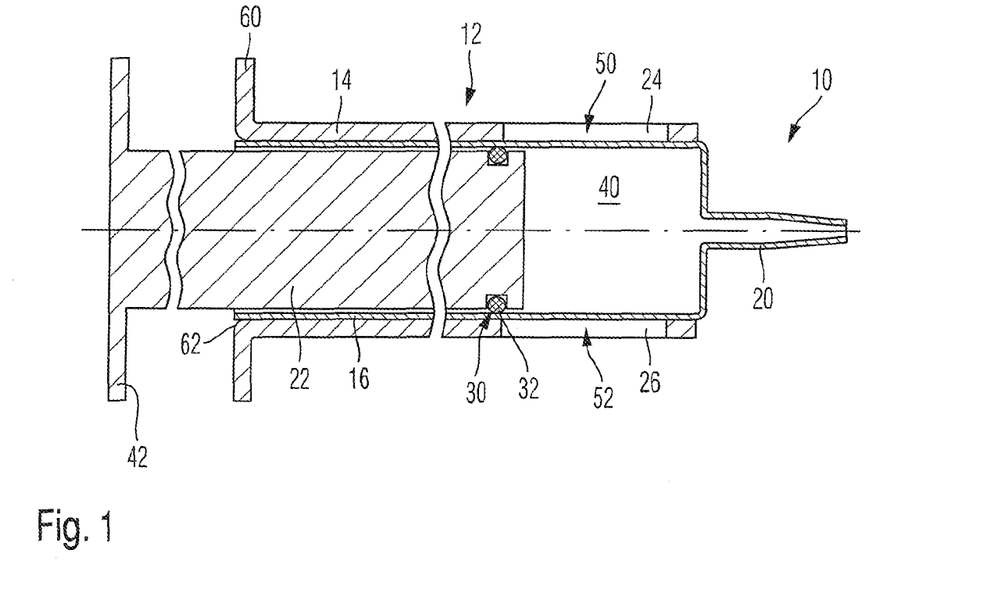
FIG. 1 a slightly schematised sectional view of an embodiment of a syringe in accordance with the invention.

Syringe 10 depicted in FIG. 1 is provided with a syringe housing 12 which is designed as two parts in the embodiment depicted.

Syringe housing 12 is provided with an outer housing 14 and an inner housing 16. Outer housing 14 has a comparatively large wall thickness of, for example, 1 mm or 2 mm. It is made out of a harder set plastics material.

Inner housing 16 can, in contrast to this, be provided with a lower wall thickness of, for instance, 0.2 to 0.3 mm. Both because of the low wall thickness and because of the selection of materials, namely a slightly softer set plastics material, inner housing 16 is of flexible design per se and is insofar deformable. However, in its predominant part it is supported by outer housing 14. The inside diameter of the outer housing corresponds to the outside diameter of inner housing 16, or is different by few p.

At the front end of syringe housing 12, an outlet cannula 20 is provided. Outlet cannula 20 is formed to be conically tapering in manner known per se, such that the area of flow cross-section on the input side of outlet cannula 20 amounts to, for example the twentyfold, preferably to approximately the sixfold, of the flow cross-section at the output end of outlet cannula 20. The inside diameter of the input end of outlet cannula 20 correspondingly amounts to approximately the two-and-a-half-fold of the inside diameter at the output end of outlet cannula 20.

In a manner also known per se, outlet cannula 20 is connected in flow connection with the cylindrical portion of syringe housing 12. The cylindrical portion ends either in a cone with a very obtuse cone angle, or flat, as is depicted in FIG. 1, in order to thus guarantee as low a degree of loss of dental material as possible. Until the end of the cylindrical portion of syringe housing 12, a plunger 22 can be inserted, in order to squeeze out the dental material that was accommodated in syringe 10 before.

In the exemplary embodiment depicted, outlet cannula 20 and the cylinder end of the cylindrical portion of syringe housing 12 are integrally designed with inner housing 16. It is to be understood that instead of this, however, any other suitable embodiment can be selected as well.

Outer housing 14 is provided with two break-throughs 24 and 26 positioned opposite of each other. With the help of these break-throughs it is guaranteed that the outer side of inner housing 16 is freely accessible at this position which is adjacent at outlet cannula 20.

Plunger 22 is provided with a diameter which essentially corresponds to the inside diameter of inner housing 16 and is slightly smaller than said, for instance by 0.1 mm. At its front end, i.e. the end facing towards outlet cannula 20, an annular groove 30 may, for example, be provided which accommodates a sealing ring 32. The outside diameter of plunger 22 with inserted sealing ring 32 is slightly larger than the inside diameter of inner housing 16, for instance by 0.2 mm or 0.3 mm. Sealing ring 32 is elastically compressible in a manner known per se and creates a sealing of the inside space 40 of syringe 10 which is filled with dental material.

Instead of this, however, an elastic cap with integrally formed sealing lips can also be provided. The sealing by sealing ring 32 is so strong that when pressure is exerted on plunger 22 with the help of gripping manubrium 42 of plunger 22, dental material is squeezed out from inside space 40 via outlet cannula 20, however, sealing ring 32 provides a sealing against inside housing 16.

Also when pressure is exerted on the exposed areas 50 and 52 of inside housing 16 under break-throughs 24 and 26, no dental material will flow past sealing ring 32. When pressure is exerted on these areas 50 and 52, plunger 22 is not pressed backwards either since the degree of friction between sealing ring 32 and inner housing 16 is sufficiently high to prevent this. Rather, this results in a precise squeezing out and outputting of dental material from outlet cannula 20.

In the embodiment depicted, outer housing 14 is provided with a circumferential collar 60 at its rear end. For actuating plunger 22, the user takes syringe 10 between his forefinger and middle finger in such a manner that the forefinger and middle finger are in contact with collar 60 starting from the front side of syringe 10. The thumb of the same hand of the user abuts against gripping manubrium 42. As a result, a one-hand operation for the quicker output of dental material can be put into practice easily in a manner known per se.

In the case of fine dosage, the grip is changed by the user. Syringe 10 is now held between thumb and forefinger exclusively at surfaces 50 and 52, whereas the backward portion of syringe 10 including gripping manubrium 42 abuts against the heel of the hand and is, if necessary, stabilised by the ring finger. With pressure between forefinger and thumb of the user, dental material can now be output in a sensitive and precise manner, and the user is positioned extremely close to the place of output with his well controllable fingers of thumb and forefinger herein when outputting the dental material, such that dosage as well as positional control are possible in a precise and exact manner.

Insofar, in accordance with the invention, despite the combination of output with larger amount as well as the fine dosage, a single-handed operation can be put into practice without the production of syringe 10 in accordance with the invention being particularly elaborate.

For the fitting of inner housing 16 on outer housing 14, these may be welded to each other at rear end 62. It is, however, also possible that inner housing 16 forms another collar there which prevents a pushing-through through outer housing 14.

Outlet cannula 20 may carry an external thread in a manner known per se outside and in the rear region, which external thread is intended to engage with an internal thread of a closing cap. Such closing caps and systems have been known for a long time and per se.

Figure 2:
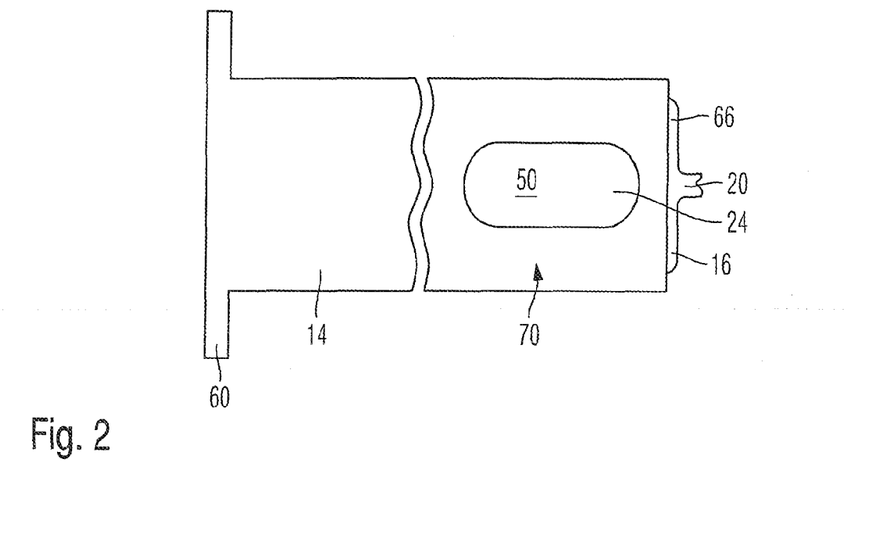
FIG. 2 a portion of the syringe in accordance with FIG. 1 in a lateral top view.

From FIG. 2 it can be taken in what manner break-through 24 extends in a grip-friendly manner and at the same time releases area 50 of inner housing 16. As can be seen, inner housing 16 protrudes slightly towards the front from the outer housing, after the radial support there is taken over by front wall 66 of inner housing 16.

The dimensioning of the materials thicknesses and flow resistances is measured such that when squeezing out dental material from inside space 40 by means of actuating plunger 22 also in the region of break-throughs 24 and 26, no overflow over sealing ring 32 occurs. For this purpose, break-throughs 24 and 26 are selected to be sufficiently small, such that a support exists also in the front region with the help of outer housing 14. Alternatively, the outer housing itself may also be kept movable in this position, for example with the help of slots which allow partial compression, or also with the help of one-sided or both-sided levers which are fitted on the outside of syringe 10 and serve for the purpose of compression.

Figure 3:
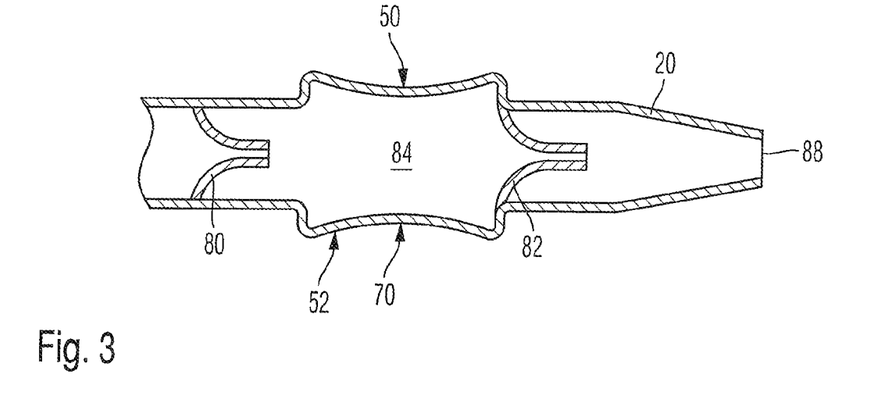
FIG. 3 another embodiment of a syringe in accordance with the invention, with a portion of said syringe depicted, namely a portion of the outlet cannula.

A further modified embodiment of the invention can be taken from FIG. 3. With this solution, the deformable region of syringe housing 12 has been translocated into outlet cannula 20 (or into the front end of the syringe near the outlet cannula). With the embodiment in accordance with FIG. 1 and FIG. 2, deformable region 70 is positioned adjacent to outlet cannula 20, while with the embodiment in accordance with FIG. 3, it is part of said. Accordingly, the entire cylindrical portion of syringe housing 12 is of dimensionally stable design and cannot, or not essentially, be deformed by the usual forces. Deformable region 70 of syringe housing 12 is in this solution provided with areas 50 and 52 which can be compressed in the direction towards each other. In the exemplary embodiment depicted, they are of finger-friendly design, but may also be of concave or convex shape. Each downstream and upstream of this deformable region 50, back-pressure valves 80 and 82 are provided.

When regions 50 and 52 are compressed, pressure is created in the inside space 84 of deformable region 70. Since back-pressure valve 80 is closing, back-pressure valve 82 is opened, and dental material can be output vie outlet end 88 of outlet cannula 20. When regions 20 and 22 are released, the material of outlet cannula 20 wants to return to its original state again, since it is elastic. Due to the effect of back-pressure valve 82, however, the dental material cannot flow back, such that back-pressure valve 80 opens and more material can flow in.

This is inhaled via inside space 40, or is pushed by means of pressure exerted onto the gripping manubrium 42 of plunger 22.

It is to be understood that with this solution, one can possibly also do without back-pressure valve 82 if a reverse flow of dental material from the outlet end should be uncritical.

Figure 4:
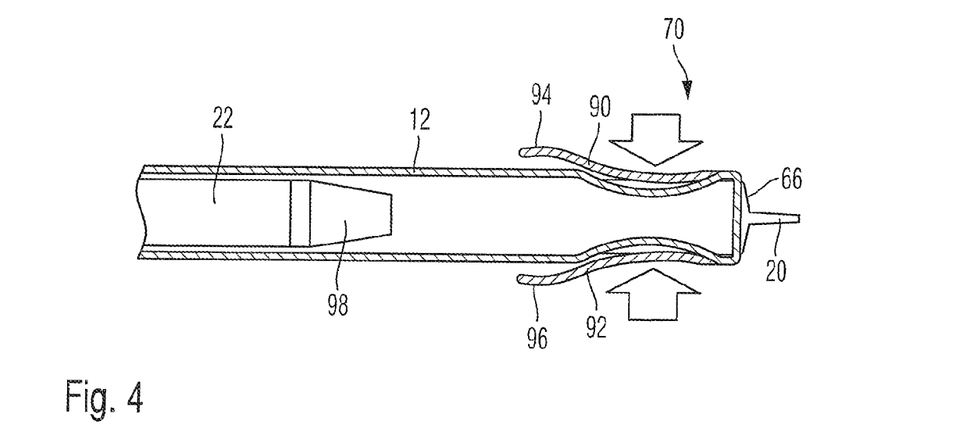
FIG. 4 a schematic view of another embodiment of a syringe in accordance with the invention.

The embodiment depicted in FIG. 4 shows a syringe 10 with which region 70 of syringe housing 12 is deformable. The deformation is effected with the help of elastic side walls of syringe housing 12 provided in region 70 which is adjacent to outlet cannula 20. Levers 90 and 92 are fitted on the front end of the cylindrical portion of syringe housing 12, adjacent to front wall 66. At this position, each lever 90 and 92 is flexibly connected with syringe housing 12 in some suitable manner. In the exemplary embodiment depicted, each lever is essentially curved in S-shape and, such that it can press onto syringe housing 12 in region 70 if pressure is exerted at remote ends 94 and 96 each onto the lever 90 and 92 concerned.

With the help of this embodiment, the output of dental material via the outlet cannula can be set even more precisely, for lever 90—and equally lever 92—acts reductively, such that a movement of ends 94 and 96 leads to a lower degree of movement in region 70.

In the exemplary embodiment depicted, levers 90 and 92 are shaped as one-armed levers, wherein the load-carrying arm is shorter than the force arm in each case.

In the exemplary embodiment depicted, plunger 22 is further provided with a cone 98 at its tip which is facing towards outlet cannula 20. This solution makes it possible to push plunger 22 forwards until abutting against front wall 66, but still deforming deformable region 70. A fine dosage is thus possible until the dental material has been completely output.

Figure 5:
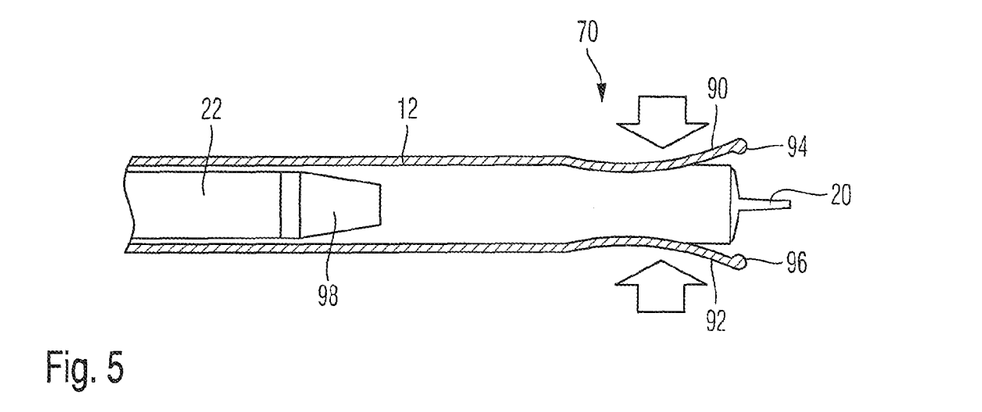
FIG. 5 a schematic view of another embodiment of a syringe in accordance with the invention.

A similar embodiment can be taken from FIG. 5. Here as well, levers 90 and 92 are provided with the help of which pressure can be reductively exerted onto deformable region 70 of syringe housing 12, wherein region 70 is again adjacent to outlet cannula 20.

Here as well, plunger 22 is provided with a cone 98 at its tip, which can enter into deformable region 70 undisturbedly.

Different from the embodiment in accordance with FIG. 4, however, with the embodiment in accordance with FIG. 5, each lever 90 and 92 is hinged at the end of deformable region 70 positioned opposite of outlet cannula 20. Correspondingly, ends 94 and 96 point in the forward direction, which is towards outlet cannula 20. Here as well, a reduction and a correspondingly precise dosage of the material output can be achieved.

Figure 6:
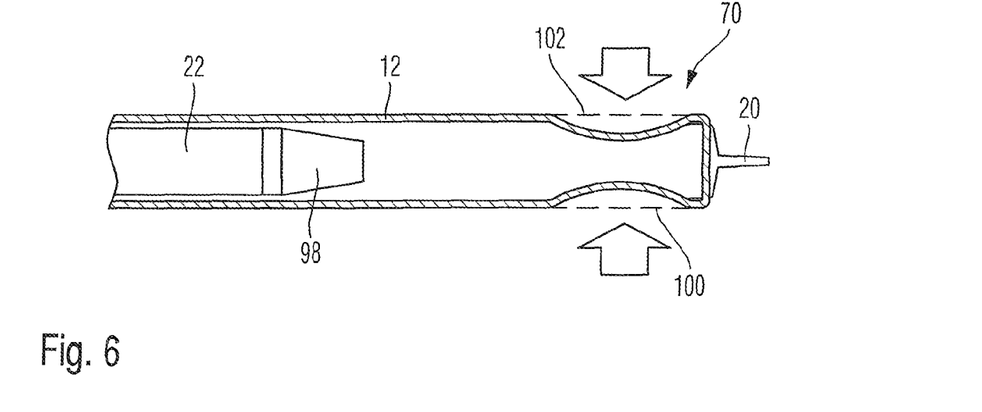
FIG. 6 a schematic view of another embodiment of a syringe in accordance with the invention.

With the embodiment in accordance with FIG. 6, it is intended to include deformable region 70 immediately into the syringe housing. Correspondingly, the syringe housing is not provided with two walls in this embodiment, as is the case with the embodiments in accordance with FIG. 1 and FIG. 2, but rather with one wall. The dimensionally stable region of syringe housing 12 is basically provided with break-throughs in accordance with break-throughs 24 and 26 of FIG. 1. However, these are closed by elastic inserts 100 and 102, such that here a well a fine dosage is possible in the manner already described.

Figure 7:
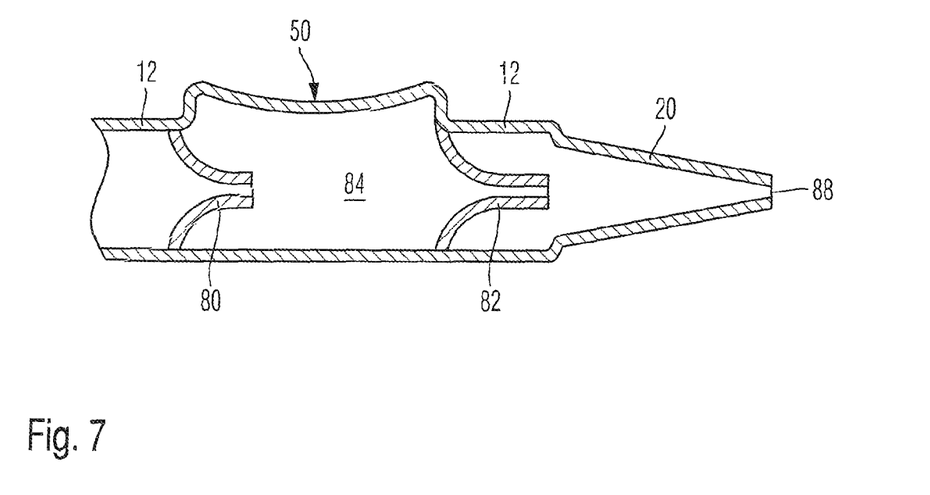
FIG. 7 a schematic view of another embodiment of a syringe in accordance with the invention.

Whereas in FIG. 1 the pump which is, for example, visible from FIG. 3 or FIG. 7, is not visible, it is to be understood that the embodiment depicted there can without any problems also be provided with a corresponding pump.

The pump depicted in FIG. 7 is provided to be actuated with one finger. Other than the embodiment in accordance with FIG. 3, actuation is possible by single-sided pressure onto area 50, wherein it is to be understood that the opposite surface which is provided in cylindrical shape is of more dimensionally stable design.

A particular advantage of this embodiment is that with the help of the two valves which surround inside space 84, pressure can be created in a particularly good manner. Also with more viscous materials which are to be expressed, the materials output can thus be precisely dosed.

It is possible to provide the elastic wall in the region of area 50 in the shape of a prominent press button; this even makes the system self-explanatory to the user.

Even if in the scope of the present exemplary embodiments, valves 80 and 82 are provided as what is referred to as duckbill valves, it is to be understood that any other designs of valves are possible just as well, for instance reed valves or blade-type valves, and basically any type of valve which automatically opens in the flow direction and automatically locks against the flow direction.

The invention claimed is:

1. Syringe for viscous or liquid dental materials comprising
   a syringe housing (12),
   a plunger (22) disposed in the syringe housing and guided in the syringe housing for displacement,
   wherein the plunger (22) can be removed from the syringe housing (12) and introduced into the housing, and
   an outlet cannula (20) fitted on the syringe housing (12),
   wherein the syringe housing (12) comprises an outer housing and an inner compressible housing,
   wherein the outer housing comprises a dimensionally stable region which is remote from the outlet cannula (20) and a deformable region which is adjacent to the outlet cannula (20),
   wherein the dimensionally stable region is not capable of being deformed,
   wherein the outer housing extends outside and around the inner compressible housing,
   wherein the inner compressible housing extends the complete length of the syringe housing (12) in which the plunger (22) is guided in the syringe housing 12, and
   wherein the inner compressible housing is insertable into the outer housing.

2. Syringe in accordance with claim 1, wherein the deformable region of the syringe housing (12) is provided with deformable side walls or side wall regions.

3. Syringe in accordance with claim 2, wherein the deformable side walls or side wall regions of the deformable region allow the plunger (22) to be introduced into the deformable region and wherein the deformable side walls or side wall regions are smaller than a dimensionally stable inside wall of the dimensionally stable region and that frictional resistance between the plunger (22) and the deformable region of the syringe housing (12) is slightly higher than frictional resistance between the plunger (22) and the dimensionally stable region of the syringe housing (12).

4. Syringe in accordance with claim 3, wherein the outlet cannula (20) is fitted on a dimensionally stable cannula support which covers a front surface of a reception capacity of the syringe (10), positioned opposite of the plunger (22), the deformable region of the syringe housing (12) extends between the cannula support and the dimensionally stable region of the syringe housing (12).

5. Syringe in accordance with claim 3, wherein the frictional resistance between the plunger (22) and the deformable region of the syringe housing (12) is higher by between 5 and 20%, than the frictional resistance between the plunger (22) and the dimensionally stable region of the syringe housing (12).

6. Syringe in accordance with claim 1, wherein the deformable region occupies a length of between 10 and 50% of the length of the syringe housing (12), and/or that the deformable region of the syringe housing (12) has a length of between 1 cm and 3 cm.

7. Syringe in accordance with claim 6, wherein the deformable region is formed by a cylindrical tube which has been inserted into the dimensionally stable region and has been captively connected with the syringe body by means of welding or gluing.

8. Syringe in accordance with claim 7, wherein the deformable region which is adjacent to the outlet cannula (20) can be squeezed together and emptied.

9. Syringe in accordance with claim 8, wherein the outlet cannula (20) is provided with a back-pressure valve which prevents the inhalation of air when the load is removed from the plunger (22) and/or from the deformable region.

10. Syringe in accordance with claim 9, wherein the dimensionally stable region of the syringe housing (12) is provided, over the deformable region of the syringe housing (12), wherein the dimensionally stable region includes an extension which extends to a support of the outlet cannula (20) and wherein regions of actuation of the deformable region of the syringe housing (12) are exposed.

11. Syringe in accordance with claim 10, wherein the syringe (10) is provided with levers which extend over the deformable region and are hinged to the dimensionally stable region, and with pressure can be exerted to the deformable region of the syringe housing (12).

12. Syringe in accordance with claim 11, wherein the levers are provided as one-sided levers and comprise free ends that extend in parallel with the longitudinal axis of the syringe (10) and point towards the outlet cannula (20).

13. Syringe in accordance with claim 12, wherein the deformable region together with the outlet cannula (20) is formed by an intrinsically single-piece and is a squeezable plastic part or compressible plastic part which has been inserted into the dimensionally stable portion of the syringe (10), wherein a deformable inside diameter of the deformable region is smaller than a dimensionally stable inside diameter of the dimensionally stable portion of the syringe housing (12).

14. Syringe in accordance with claim 11, wherein the levers are provided as one-sided levers and comprise free ends that extend in parallel with the longitudinal axis of the syringe (10) and point backwards.

15. Syringe in accordance with claim 1, wherein the deformable region occupies a length of between 15 and 30% of the length of the syringe housing (12), and/or that the deformable region of the syringe housing (12) has a length of approximately 2 cm.

16. Syringe in accordance with claim 1, wherein the deformable region occupies a length of between 20 and 25% of the length of the syringe housing (12).

17. Syringe for viscous or liquid dental materials comprising
a syringe housing (12),
a plunger (22) disposed in the syringe housing and guided for displacement,
wherein the plunger (22) can be removed from the syringe housing (12) and introduced into the housing, and
an outlet cannula (20) fitted on the syringe housing (12),
wherein the syringe housing (12) comprises an outer housing and an inner compressible housing,
wherein the outer housing comprises a dimensionally stable region which is remote from the outlet cannula (20) and a deformable region which is adjacent to the outlet cannula (20),
wherein the dimensionally stable region is not capable of being deformed,
wherein the outer housing extends outside and around the inner compressible housing,
wherein the deformable region is provided with a pump,
wherein the inner compressible housing is insertable into the outer housing, and
wherein the inner compressible housing extends the complete length of the syringe housing (12) in which the plunger (22) is guided in the syringe housing 12.

18. Syringe for viscous or liquid dental materials in accordance with claim 17 in combination with a more viscous material or a more liquid material, wherein deformability of the deformable region is adapted to the viscosity of the dental material, and the deformable region of the syringe housing (12) exhibits a lower degree of elasticity with the use of a more viscous material and a higher degree of elasticity with the use of a more liquid material.

* * * * *